US012339339B2

(12) United States Patent
Sommer et al.

(10) Patent No.: US 12,339,339 B2
(45) Date of Patent: Jun. 24, 2025

(54) METHOD AND SYSTEM FOR T1 MAPPING FOR TISSUE CHARACTERIZED BY SHORT-T2 RELAXATION IN MRI

(71) Applicants: Siemens Healthcare GmbH, Erlangen (DE); Balgrist Campus AG, Zürich (CH)

(72) Inventors: Stefan Sommer, Zürich (CH); Tom Hilbert, Lausanne (CH); Daniel Nanz, Hombrechtikon (CH)

(73) Assignees: Siemens Healthcare GmbH, Erlangen (DE); Balgrist Campus AG, Zürich (CH)

( * ) Notice: Subject to any disclaimer, the term of this patent is extended or adjusted under 35 U.S.C. 154(b) by 64 days.

(21) Appl. No.: 18/298,515

(22) Filed: Apr. 11, 2023

(65) Prior Publication Data
US 2023/0333186 A1 Oct. 19, 2023

(30) Foreign Application Priority Data

Apr. 14, 2022 (EP) .................................. 22168302

(51) Int. Cl.
*G01V 3/00* (2006.01)
*A61B 5/055* (2006.01)
(Continued)

(52) U.S. Cl.
CPC .............. *G01R 33/50* (2013.01); *A61B 5/055* (2013.01); *G01R 33/5608* (2013.01)

(58) Field of Classification Search
CPC ...... G01R 33/50; G01R 33/5608; A61B 5/055
(Continued)

(56) References Cited

U.S. PATENT DOCUMENTS 9,759,795 B2 * 9/2017 Liu .................... G01R 33/5602
10,132,898 B2 * 11/2018 Kecskemeti ....... G01R 33/5602
(Continued)

FOREIGN PATENT DOCUMENTS

EP 1405107 B1 * 7/2011 ........... G01N 24/081

OTHER PUBLICATIONS

Jiang Du* and Graeme M. Bydder, Qualitative and quantitative ultrashort-TE MRI, of cortical bone, (wileyonlinelibrary.com) DOI: 10.1002/nbm.2906, NMR Biomed. 2013; 26: 489-506; 2013.
(Continued)

*Primary Examiner* — Walter L Lindsay, Jr.
*Assistant Examiner* — Frederick Wenderoth
(74) *Attorney, Agent, or Firm* — Laurence A. Greenberg; Werner H. Stemer; Ralph E. Locher

(57) ABSTRACT

An MRI method and system for mapping T1 relaxation times of a biological object with a part having a short-T2 relaxation time. The MRI system first performs one or several magnetization preparation radio frequency pulse sequences, with successive RF pulse sequences being separated by a repetition time interval TR. The MRI system acquires an MRI signal generated by the part of said biological object during each repetition time interval TR in response to a plurality of 3D readout blocks generated by the MRI system and applied to the part of the biological object. For each readout block, an MRI signal is acquired by the MRI system at a different recovery time. Each readout block is sensitive to short-T2 signal. An image of the part is reconstructed from each MRI signal and T1 values are mapped for the part from at least two of said reconstructed images.

9 Claims, 3 Drawing Sheets

(51) Int. Cl.
*G01R 33/50* (2006.01)
*G01R 33/56* (2006.01)

(58) Field of Classification Search
USPC .......................................................... 324/309
See application file for complete search history.

(56) References Cited

U.S. PATENT DOCUMENTS

| | | | | |
|---|---|---|---|---|
| 2015/0268316 | A1* | 9/2015 | Seethamraju | G01R 33/4816 |
| | | | | 324/309 |
| 2017/0102439 | A1* | 4/2017 | McMillan | G01R 33/4816 |
| 2018/0231626 | A1* | 8/2018 | Gulani | G01R 33/4826 |
| 2019/0279358 | A1* | 9/2019 | Schaal | A61B 3/102 |

OTHER PUBLICATIONS

Simon M.F. Triphan, Oxygen Enhanced Lung MRI by Simultaneous, Measurement of T1 and T2* During Free, Breathing Using Ultrashort TE, Journal of Magnetic Resonance Imaging 41:1708-1714 (2015); 2015.

Steven D. Beyea, Relaxation Time Mapping of Short T*, 02 Nuclei, with Single-Point Imaging (SPI) Methods, Journal of Magnetic Resonance 135, 156-164 (1998), Article No. MN981537; 1998.

Qing Li, Ultrashort echo time magnetic resonance fingerprinting, (UTE-MRF) for simultaneous quantification of long and, ultrashort T2 tissues, Magn Reson Med. 2019;82:1359-1372; 2019.

Fabian Springer, Magnetization Transfer Contrast Imaging in Bovine and, Human Cortical Bone Applying an Ultrashort Echo Time, Sequence at 3 Tesla, Magnetic Resonance in Medicine 61:1040-1048 (2009); 2009.

Zhao Wei, Fast T1 measurement of cortical bone using 3D UTE actual flip, angle imaging and single-TR acquisition (3D UTE-AFI-STR), Magn Reson Med. 2021;85:3290-3298.; 2021.

Weiger, M., et al., Short-T2 MRI: Principles and recent advances. Prog Nucl Magn Reason Spectrosc, 2019. 114-115: p. 237-270.

José P. Marques, MP2RAGE, a self bias-field corrected sequence for improved segmentation, and T1-mapping at high field NeuroImage 49 (2010) 1271-1281; 2010.

Qi Haikun et al., "Simultaneous T1 and T2 mapping of the carotid plaque (SIMPLE) with, T2 and inversion recovery prepared 3D radial imaging", Magnetic Resonance In, Medicine, vol. 80, No. 6, May 25, 2018 (May 25, 2018), pp. 2598-2608, XP55964973.

Zhao Wei, Ya-Jun Ma A, Hyungseok Jang A, Wenhui Yang B,C, To measure T1 of short T2 species using an inversion recovery prepared; three-dimensional ultrashort echo time (3D IR-UTE) method: A phantom; study; Journal of Magnetic Resonance 314 (2020) 106725; 2020.

Jiang Du, Qualitative and quantitative ultrashort echo time (UTE) imaging of cortical bonej; Journal of Magnetic Resonance 207 (2010) 304-311; 2010.

Tan Guo, T1 measurement of bound water in cortical bone using 3D; adiabatic inversion recovery ultrashort echo time (3D IR-UTE), Cones imaging, Magn Reson Med. 2019;00:1-12. wileyonlinelibrary. com/journal/mrm © 2019 International Society for Magnetic, Resonance | 1; 2020.

Ya-Jun Ma et al., Whole knee joint T1 values measured in vivo at 3T by combined, 3D ultrashort echo time cones actual flip angle and variable flip, angle methods, Magn Reson Med. 2019;81:1634-1644.; 2019.

Matthew F. Glasser, et al, The minimal preprocessing pipelines for the Human Connectome Project; NeuroImage, 2013. 80: p. 105-124. https://www.sciencedirect.com/science/article/abs/pii/S1053811913005053?via%3Dihub;; 2013.

Ryan Chamberlain et al., "Measuring T1 in the presence of very high iron, concentrations with Swift", Proceedings of the International Society for, Magnetic Resonance in Medicine, ISMRM, 20th Annual Meeting and, Exhibition, Melbourne, Australia, May 5-11, 2012, Apr. 21, 2012 (Apr. 21, 2012), XP040626789.

Misung Han et al., "Actual Flip Angle Imaging to Improve T1 Measurement for Short T2, Tissues", Proceedings of the International Society for Magnetic, Resonance in Medicine, ISMRM, 23rd Annual Meeting and Exhibition, Toronto, Ontario, Canada, May 30-Jun. 5, 2015, No. 501, May 15, 2015 (May 15, 2015), XP040666184.

Jun Chen, Measurement of Bound and Pore Water T1 Relaxation, Times in Cortical Bone Using Three-Dimensional, Ultrashort Echo Time Cones Sequences, Magnetic Resonance in Medicine 77:2136-2145 (2017); 2017.

Mark Oliver Wielputz et al., Outracing Lung Signal Decay— Potential of Ultrashort Echo Time MRI, Dem Signalzerfall in der Lunge zuvorkommen—Potenzial der, Ultrashort-Echo-Time-MRT, Wielpütz Mo et al. Outracing Lung Signal . . . Fortschr Röntgenstr 2019; 191: 415-423; 2019.

Djaudat Idiyatullin et al., Fast and quiet MRI using a swept radiofrequency, Journal of Magnetic Resonance, 2006, pp. 342-349, vol. 181, Elsevier.

* cited by examiner

METHOD AND SYSTEM FOR T1 MAPPING FOR TISSUE CHARACTERIZED BY SHORT-T2 RELAXATION IN MRI

CROSS-REFERENCE TO RELATED APPLICATION

This application claims the priority, under 35 U.S.C. § 119, of European Patent Application EP 22168302.2, filed Apr. 14, 2022; the prior application is herewith incorporated by reference in its entirety.

FIELD AND BACKGROUND OF THE INVENTION

The present invention lies in the field of magnetic resonance imaging (MRI) systems and methods. In particular, the present invention relates to a method and system for magnetic resonance imaging in which a magnetization preparation radio frequency pulse sequence is used together with a 3D image sampling readout sensitive to short time constant T2 or T2* (i.e., the time constant for the decay of transverse magnetization arising from natural interactions at the atomic or molecular levels), and to a device for carrying out the method. The many considerations hold equally for different types of signal decay and therefore, unless stated otherwise, all kinds of rapid loss of transverse magnetization (whether best characterized by T2 or T2*) will be jointly referred to as short-T2 [1] decay (or simply "short-T2") thereafter. In particular, the present invention is interested in mapping the longitudinal relaxation time T1 for biological matter characterized by a short-T2 relaxation time.

Magnetic resonance imaging (MRI) is a powerful technique that is capable of providing detailed images of a biological body, such as a human body.

The signal detected in medical MRI is proportional to the transversal 1H nuclear spin magnetization. Once generated, it decays approximately exponentially with time constants T2* (transverse magnetization decay effectively observed during MRI experiments, e.g., in gradient-echo (GRE) or free-induction-decay sequences, with $T2^* \leq T2$). The 1H transverse relaxation times in small molecules in liquids, but also in water molecules in most soft tissues, are relatively long, i.e., in the order of tens of milliseconds up to seconds. A much faster signal decay can be observed in molecules with more restricted mobility—caused by a geometrically restricted environment—such as observed with water protons in tendons or bone—or by a larger molecular size and mass and concomitantly slowed molecular rotation and translation—such as in macro-molecules. The acquisition of short-T2 signals (T2<1 ms) can be achieved by a very fast spatial encoding and by the omission of an echo generation, i.e., by direct sampling of the free induction decay (FID) after the application of a radiofrequency excitation pulse. Numerous MRI sequences defined by different use of radio frequency (RF) pulses and magnetic gradient fields (gradients) used for spatial encoding are well-known to the persons skilled in the art. Techniques that enable the detection of short-T2 signal components include among others e.g., ultra-short echo time (UTE), zero echo time (ZTE) or single-point imaging (SPI) methods.

The contrast and signal intensity in a conventional MR image depend on a variety of physical, chemical, and physiological parameters of the observed tissue, as well as on the acquisition technique: a complex and—typically unknown and ill-controlled—mix of these factors can produce different signal intensities or even contrast weightings and preclude reliable reproduction. The mean signal value within a region of interest within the same tissue may vary across values measured on scanners from different vendors at different sites, but even in immediate test-retest repeated acquisitions of the same individual on the same scanner.

A more quantitative approach at characterizing biological tissue by MRI is to directly measure one or more of the physical tissue properties in isolation, separating its/their influence on the complex mix that determines signal intensity and contrast in traditional images. Such techniques are usually referred to as "parametric mapping" or "quantitative imaging/qMRI" methods. They can produce quantitative parametric tissue maps that less strongly depend on the employed hardware, the applied imaging technique, and the image-acquisition parameters.

The move from relative contrast information that depends on a variety of factors to a single, absolute measure based on physical tissue properties is a prerequisite, e.g., for the comparability of values (i) measured at different points in time in a single individuum in longitudinal studies, e.g., to monitor and quantify disease progress or therapy response or (ii) measured with different scanners, at different institutions and/or in different individuals. It may enable the establishment of databases of normal quantitative tissue values, to which a newly scanned patient dataset can be compared, and even contribute to an improved single-individual's diagnosis based on a single scan.

One tissue parameter of interest is T1. The most basic and probably most accurate approach for quantitative T1 mapping are repeated inversion-recovery (IR) experiments in combination with a spin-echo (SE) sequence. After an (adiabatic) inversion pulse, the longitudinal magnetization exponentially approaches the equilibrium magnetization with the time constant T1. The acquisition of multiple spin-echo images, produced by data acquired at different inversion times (TI), with a repetition time (TR) that was at least 4 times as long as the longest T1 time to be measured, allows to obtain an accurate estimate of T1 from a fit of the inversion-recovery signal-model to the experimental data. However, this combination results in long, clinically impractical acquisition times, similar to T2 mapping with a single SE sequence.

One of the most promising 3D T1-mapping methods [2] is the MP2RAGE sequence [3], which was originally developed to generate T1 weighted images free from bias introduced by B1-field inhomogeneity. It implements a 2-point inversion-recovery approach with significantly shortened scan time compared to an extended inversion-recovery sampling. It periodically samples partial image data in 2 phase-encoded GRE trains that start at 2 different TI times after periodically applied 180-degree inversion pulses. During the image reconstruction, these data sets can be combined in a way that cancels the B1-strength bias and can produce images whose signal intensity directly, but non-linearly depends on a tissue's T1 time. Based on well-established simulations of the spin behavior, i.e., by Bloch simulations, such images can be converted into quantitative T1 maps.

However, components in the MR-signal from—at microscopic level—structurally rigid biological objects, such as cortical and trabecular bone, tendon, ligament, or myelin, as well as from regions with locally strongly varying magnetic susceptibility, e.g., in the lung, exhibit a fast decay (i.e., short-T2 time) that prevents detection and localization with traditional, echo-formation based MRI sequences, and, thus, that their associated quantitative properties cannot be measured. For instance, quantitative 3D T1 mapping of short-T2 signal components with clinically useful accuracy in clinically practical scan times is an unsolved problem. Also, state-of-the art T1 mapping techniques for tissues with short-T2 signal components are strongly sensitive to B1-inhomogeneity, which can result in distortion and bias of the quantitative measurements and in increased coefficients of variation for reproduction attempts. Another problem is to selectively quantify T1 times of short-T2 signal components, without interference and/or admixture from longer-T2 components. Thus, it is an interfering problem—but also a source of information—that the T1 times measured in the above-mentioned structures and tissues depend on the echo time at which signals are measured.

To summarize, 3D mapping of T1 of tissues with short-T2 signal components, combined 3D mapping of T1 and T2* of tissues with short-T2 signal components, and combined mapping of T1, T2* and magnetic susceptibility (QSM, quantitative susceptibility mapping) of tissues with short-T2 signal components are unsolved problems. Also, mapping T1 in short-T2 tissue has been shown in time consuming 2D acquisitions (look-locker) for single slices, but not in 3D. Most traditional T1 mapping methods measure signal echoes, generated by gradient refocusing alone or in coincidence with RF-induced spin echoes. The echo formation takes a minimum time, e.g., approx. 0.7 ms for GRE readouts, and 6 ms for SE readouts. By the time the data is acquired, signal components with short-T2 (<1 ms) times of the transverse magnetization will have decayed by significant amounts and may not be acquired at all. Therefore, it is not possible to measure T1 of these tissue types with most known sequences. All attempts that have been performed for quantifying T1 times of biological tissues characterized by short-T2 relaxation times have had limited success. In particular, Saturation-Recovery UTE [4,5], IR-UTE [6,7], 2D IR-UTE at varying TE [8,9], SPI [10], and 3D UTE-AFI-STR [11] are strongly hampered by inefficient data acquisition and long scan times not suitable for clinical applications, as well as by B1-inhomogeneity. Other existing solutions are even more strongly affected by B1-inhomogeneity, which requires calibration measurements and RF flip angles with high specific absorption rate (SAR), which acerbates another potential problem, i.e., high SAR values. The correction for spatially varying actual flip angle makes such techniques especially fragile at high or ultra-high field strength. Such techniques are for instance UTE-variable flip angle (VFA) [12], UTE-variable TR [13], UTE-actual flip angle (AFI) [14], 3D UTE-AFI-STR [11], or 2D UTE-Fingerprinting [15].

SUMMARY OF THE INVENTION

It is accordingly an object of the invention to provide a method and system which overcomes the above-mentioned and other disadvantages of the heretofore-known devices and methods of this general type and which provides for a system and method capable of mapping T1 times for biological matter characterized by short-T2 relaxation times and that is suitable for clinical applications.

With the above and other objects in view there is provided, in accordance with the invention, a magnetic resonance imaging (MRI) method for mapping, with an MRI system, T1 relaxation times of a biological object having a part that is characterized by a short-T2 relaxation time, the method comprising: performing, by the MRI system, one or a plurality of magnetization preparation radio frequency (RF) pulse sequences, with two successive magnetization preparation RF pulse sequences being separated by a repetition time interval TR;

acquiring, by the MRI system and during each repetition time interval TR, an MRI signal generated by the part of the biological object in response to a number N of 3D readout blocks R_i generated by the MRI system and applied to the part of the biological object, wherein for each readout block R_i, an MRI signal S_i is acquired by the MRI system at a different recovery time T_i, and wherein each readout block R_i is configured to be sensitive to short-T2 signal, and wherein i=1, . . . , N, and N≥2; and reconstructing, from each MRI signal S_i at various T_i, an image of the part and mapping T1 values for the part from two or more of the reconstructed images.

In other words and with more exemplary detail, the present invention concerns notably an MRI method for mapping T1 relaxation times of a biological object comprising a part characterized by a short-T2 relaxation time (i.e., smaller than 1 ms). The novel method comprises the following steps:

performing, by an MRI system, one or several magnetization preparation RF pulse sequences, wherein two successive magnetization preparation RF pulse sequences are separated by a repetition time interval TR;

acquiring, by the MRI system and during each repetition time interval TR, an MRI signal generated by said part of the biological object in response to N 3D readout blocks R_i generated by the MRI system and applied to said part of the biological object, wherein for each readout block R_i, an MRI signal S_i is acquired by the MRI system at a different recovery time T_i (e.g., inversion- or saturation-recovery time), and wherein each readout block R_i is configured for being sensitive to short-T2 signal, with i=1, . . . , N, with N≥2. In other words, the MRI signal generated by said part is observed by N readout blocks R_i, each centered at a different recovery time T_i and associated to an MRI signal S_i that is the set of MRI data acquired during said readout block R_i and used then for image reconstruction. The so-called "MRI signal generated by said part" comprises thus all said sets of MRI data that are acquired during the different readout blocks R_i. In particular, "sensitive to short-T2 signal" means that the 3D readout block R_i comprises a data collection of at least one echo time TE, wherein the collected data are sensitive to short-T2 signal, such a 3D readout block R_i being notably configured for acquiring signal with an echo-time TE smaller or equal to 0.7 ms. A TE of 0.7 ms is able to capture half of the MRI signal amplitude for a T2* relaxation time of 1 ms. For shorter T2* relaxation time, even shorter TE are necessary to capture enough signal. Examples of 3D readout blocks sensitive to short-T2 signal are the 3D UTE pulse sequence, or the 3D ZTE pulse sequence, or the SPI pulse sequence;

reconstructing, from each MRI signal S_i, an image of said part and mapping T1 values for said part from at least two reconstructed images. Thus, two or more reconstructed images, e.g., at least a part of their raw data, might be combined into a T1 map. In particular, instead of, or additionally to, combining two or more of the reconstructed images for extracting information about biological object tissue with short-T2 relaxation time, T1 and/or T2* information might be directly extracted from two or more of said reconstructed images by fitting an analytical model on each of said one or several reconstructed images.

According to the present invention, and preferably, each readout block $R\_i$, and thus respectively its corresponding acquired signal $S\_i$, is separated from a next readout block $R\_i+1$, and thus respectively from a next acquired signal $S\_i+1$, by a time interval (strictly) greater than 0.

According to a preferred embodiment, the N readout blocks form a continuous readout excitation pulse sequence R_cont configured for being executed by the MRI system, wherein each readout block is immediately followed by a next readout block to create continuity, the MRI signals $S\_i$, which can in this case temporally overlap (e.g., using a time-shifting reconstruction process over the continuously sampled data for R_cont, wherein temporal windows for the different MRI signals $S\_i$ may overlap—see FIG. 4), being acquired at said different recovery times $T\_i$ in order to enable the creation or reconstruction of said images of said part at different recovery times $T\_i$. Said continuous readout excitation pulse sequence R_cont might be defined as a merging of the N readout blocks into a single continuous block, wherein a temporal succession of two directly successive readout blocks is configured for creating a continuity over the so-called continuous readout excitation pulse sequence.

Optionally, different T1 maps might be generated from at least two MRI signals $S\_i$, i.e., from at least two readout blocks $R\_i$, wherein each readout block $R\_i$ comprises a collection of data at multiple echo times $TE\_j$, enabling each to estimate one of said different T1 maps. For instance, each readout block $R\_i$ comprises a train of RF excitation pulses of predefined flip angle, each followed by M gradient echoes, resulting thus in an additional dimension in the acquired MR signal denoted as $S\_i,j$, with $i=1, \ldots, N$, with $N \geq 2$ and $j=1, \ldots, M$, with $M \geq 1$. In other words, each signal $S\_i$ might comprise one or several signals $S\_i,j$, each acquired at a different echo time TE.

The present invention concerns also an MRI system or apparatus configured for mapping T1 relaxation times of a biological object comprising at least one part characterized by a short-T2 relaxation time, and configured for carrying out the steps of the previously described method.

The foregoing has broadly outlined the features and technical advantages of the present disclosure so that those skilled in the art may better understand the detailed description that follows. In other words, additional features and advantages of the disclosure will be described hereinafter that form the object of the claims. Those skilled in the art will appreciate that they may readily use the concept and the specific embodiment disclosed as a basis for modifying or designing other structures for carrying out the same purposes of the present disclosure.

Other features which are considered as characteristic for the invention are set forth in the appended claims.

Although the invention is illustrated and described herein as embodied in a method and system for T1 mapping for tissue characterized by short-T2 relaxation in MRI, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
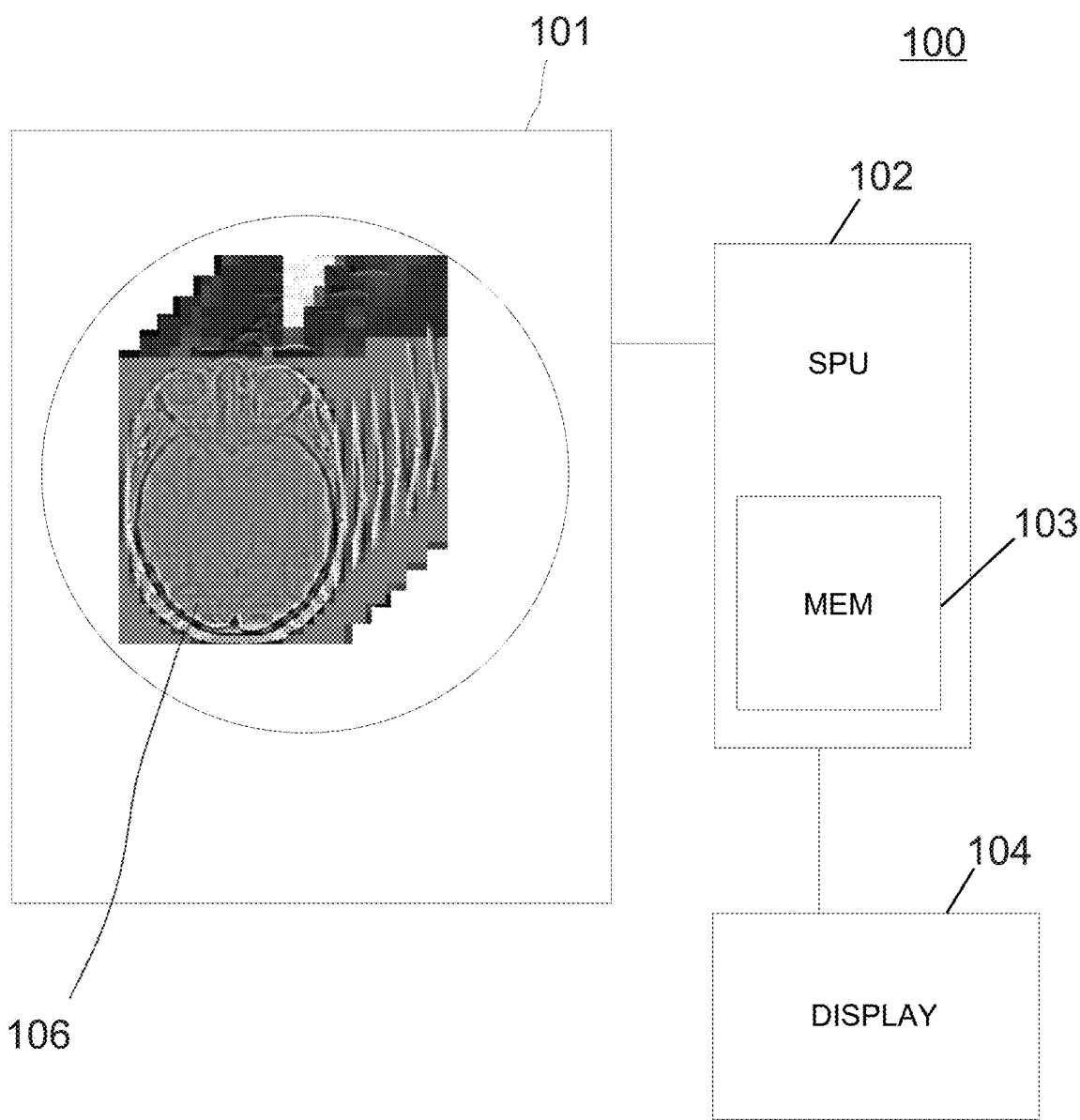
FIG. 1 is a schematic illustration of an MRI system according to the invention.
Figure 2:
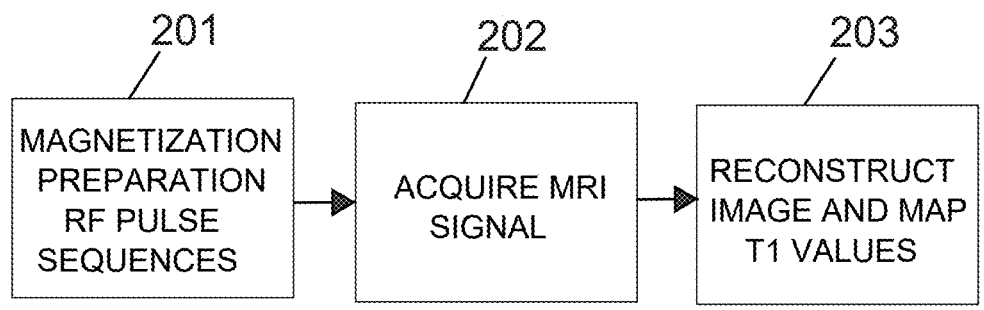
FIG. 2 illustrates a flowchart of a method according to the invention.

Referring now to the figures of the drawing in detail and first, in particular, to FIG. 1 thereof, there is shown a preferred embodiment of an MRI system 100 according to the invention, i.e., a system that is capable of imaging biological material characterized by a short-T2 relaxation time during clinical operation. The MRI system 100 comprises notably different coils 101 and respective coil controllers configured for generating magnetic fields and RF pulses in order to acquire an MRI signal from a biological object 106 comprising at least one part characterized by said short-T2 relaxation time. For instance, the MRI system 100 comprises:

an axial magnetic field coil and an axial magnetic field coil controller for controlling an axial magnetic field $B_0$ generated by said axial magnetic field coil;

a gradient coil and a gradient coil controller configured for controlling a magnetic field gradient G generated by said gradient coil;

a RF coil and a RF coil controller configured for controlling a RF magnetic field B1 produced by the RF coil;

a receiver coil, which can be the same as the RF coil, configured for detecting changes in a magnetization of the biological object 106 to be imaged, and for communicating said changes to a receiver coil controller, which can be the same as the RF coil controller, the latter outputting an MRI signal to a processing unit (SPU) 102 comprising a processor and a memory 103, the processing unit 102 being configured for processing the outputted MRI signal in order to reconstruct images of said biological object;

a display 104 for displaying the reconstructed images.

In contrast with prior art MRI systems, the MRI system 100 according to the invention is configured for carrying out the following method described in connection with FIGS. 2 to 5.

At step 201, the MRI system 100 performs one or several magnetization preparation RF pulse sequences 301. Preferably, the performed magnetization preparation RF pulse sequence is an inversion or saturation recovery pulse sequence. As known in the art, two successive magnetization preparation RF pulse sequences 301 are separated by a repetition time interval TR (see for instance FIG. 3-5). Of course, another magnetization preparation (e.g., Magnetization Transfer preparation or T2 preparation) or a combination of different preparation modules to further manipulate the signal of short-T2 signal components can be used. For example, the magnetization preparation RF pulse sequence 301 may comprise a tailored preparation pulse to suppress long-T2 signal components and, thus, selectively observe properties of short-T2 components.

Figure 3:
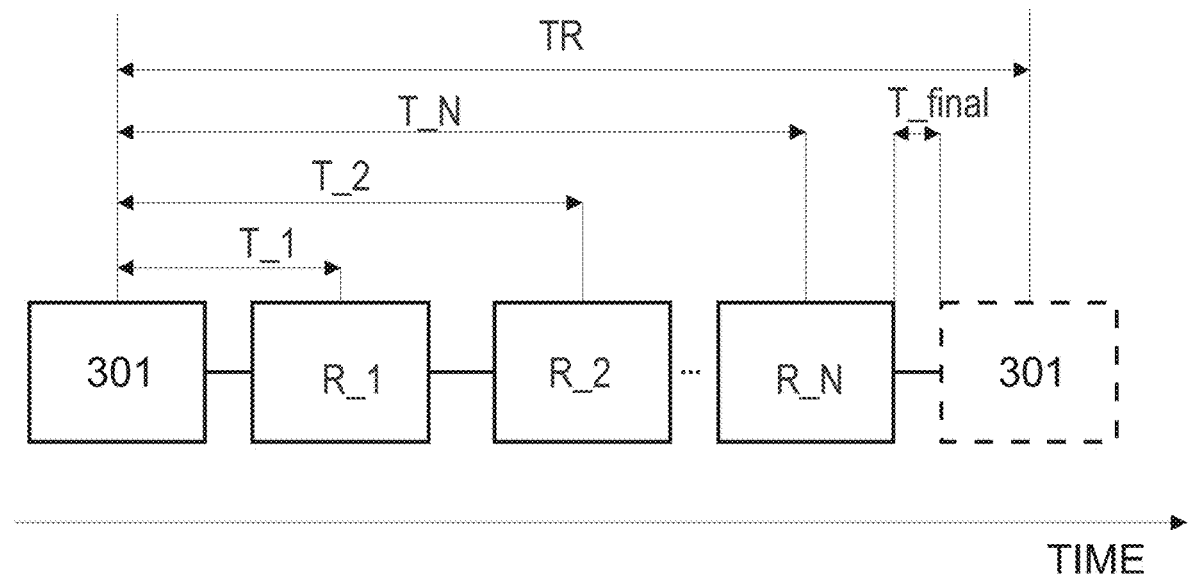
FIG. 3 shows a first preferred embodiment of a readout block according to the invention.
Figure 4:
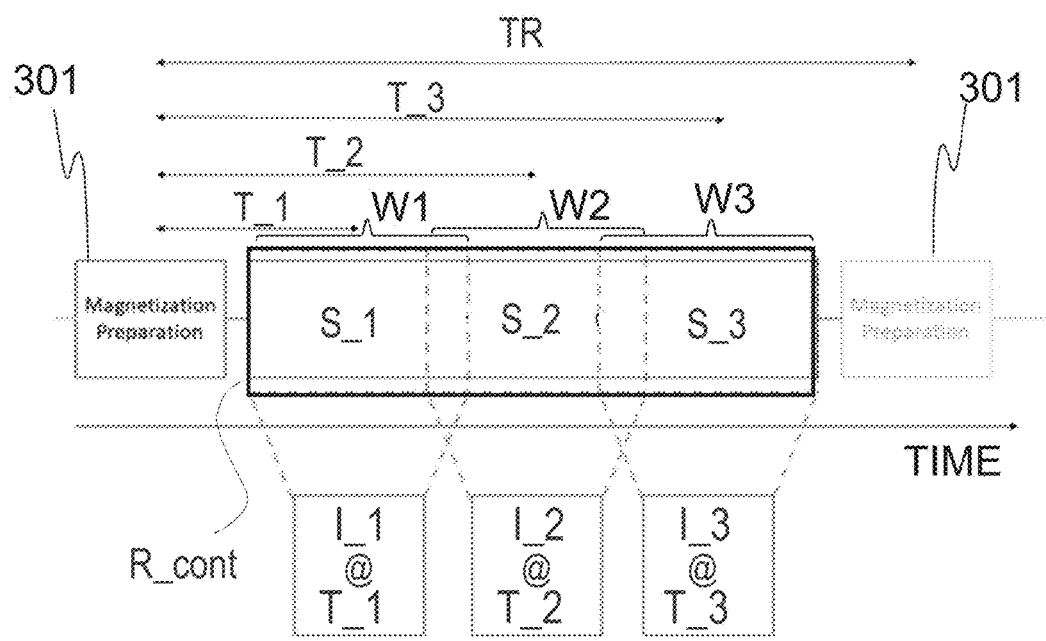
FIG. 4 shows a second preferred embodiment of a readout block according to the invention.
Figure 5:
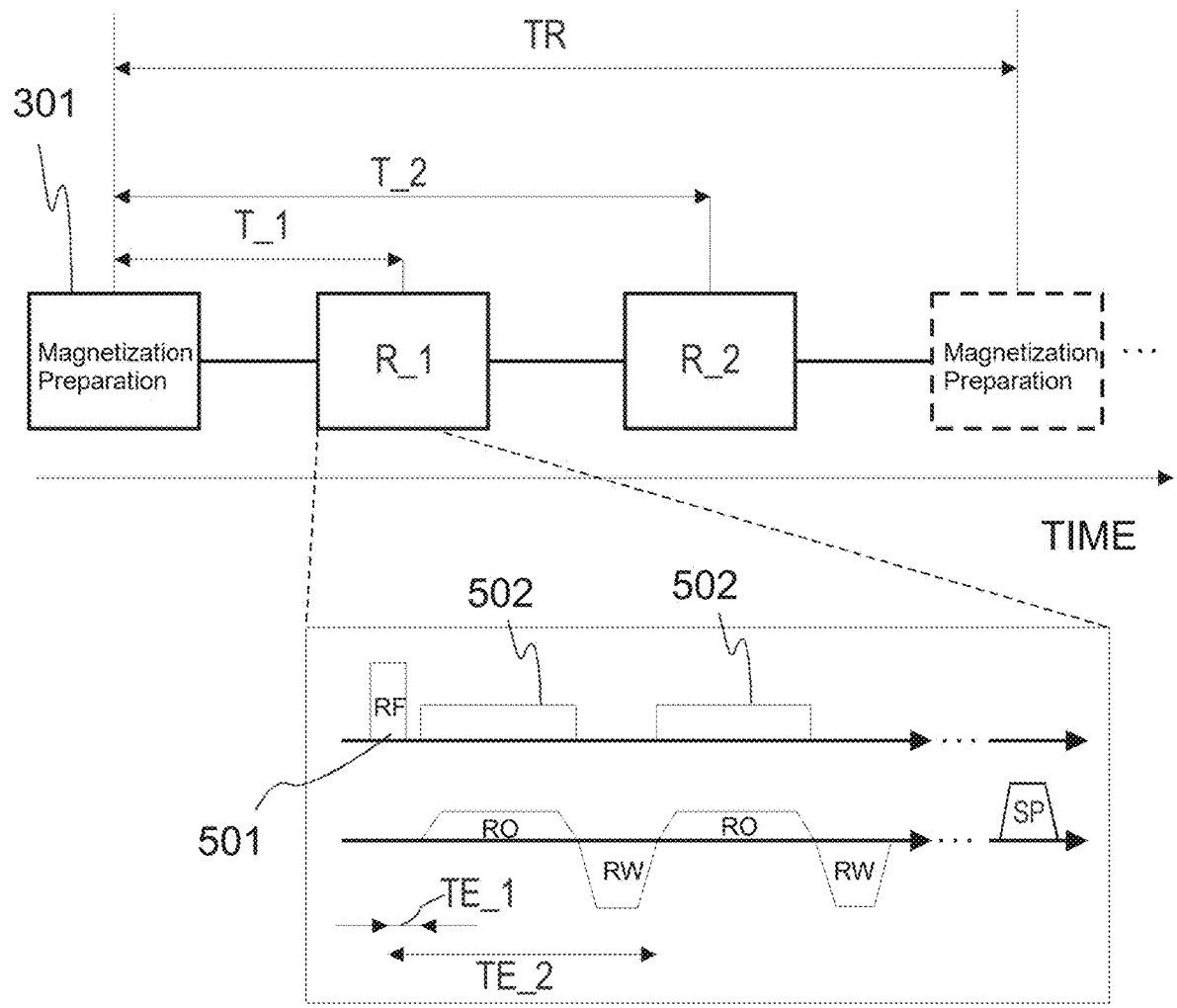
FIG. 5 shows a third preferred embodiment of a readout block according to the invention.

At step 202, the MRI system 100 acquires an MRI signal generated by said part of the biological object 106 in response to N 3D readout blocks R_i generated by the MRI system 101 and applied to said part of the biological object 106 (see FIG. 3), wherein i=1, . . . , N, and N≥2. FIG. 4 shows a preferred embodiment wherein N=3, i.e., 3 readout blocks R_1, R_2, and R_3, are successively generated and applied to the biological object 106. FIG. 5 shows another preferred embodiment wherein N=2, i.e., two readout blocks R_1 and R_2 are used. As known in the art, the first readout block R_1 starts at the recovery time T_1 after the starting-time of the magnetization preparation pulse sequence 301, each additional successive readout block R_k, with k=2, . . . , N, starting at a recovery time T_k≠T_i for i≠k, the end-time of the $N^{th}$ readout block R_N being separated from the starting-time of the next magnetization preparation pulse sequence 301 by a final recovery time T_final (see FIG. 3). As shown in FIG. 3, the recovery time T_i might also be measured from the center of the magnetization preparation pulse sequence to the center of the readout block R_i.

The readout blocks R_i take thus place during each repetition time interval TR, after a magnetization preparation RF pulse sequence and before a directly next magnetization preparation RF pulse sequence. For and during each readout block R_i, an MRI signal S_i is acquired by the MRI system 100. Said MRI signals S_i are thus acquired at the different recovery times T_i and enable to reconstruct, for each readout block, at least one MRI image from the acquired MRI signal. Preferentially, the readout blocks are separated from each other by a predefined positive period of time, so that each MRI signal S_p is acquired separately from the next MRI signal S_p+1, p=1, . . . , N−1. Contrary to most traditional MRI techniques, each readout block R_i according to the invention is configured for being sensitive to short-T2 signal.

At step 203, the MRI system 100, e.g., its processing unit 102 or a stand-alone computer device connected to the MRI system 100, is configured for reconstructing, from each MRI signal S_i, an image of said part of the biological object 106 and for using one or several of the reconstructed images for mapping T1 values for said part.

In a preferred embodiment of the invention, an acquisition of two or more images might be interleaved in a single repetition time interval TR. For instance, the MRI recovery signal is sampled (using for instance radial sampling) by two (N=2) readout blocks R_1 and R_2 of excitation-pulse/detection period combinations (e.g., 3D UTE or ZTE readout), centered or starting respectively each at a different preparation-recovery time, respectively T_1 and T_2, after the magnetization preparation (e.g., inversion or saturation) pulse sequence. Thus, during the first readout block R_1, a first MRI signal S_1 is acquired at T_1, and during the second readout block R_2, a second MRI signal S_2 is acquired at T_2, T_i being the starting time or center time of the acquisition. The signals S_1 and S_2 can then be separately reconstructed to yield "original" or "directly measured" 3D images of the observed part of the biological object 106. Said original images and/or their raw data might be suitably combined to yield quantitative estimates of localized T1 and proton-density values of the observed part (i.e., T1 and PD maps). FIG. 3 shows a generalization of the preferred embodiment using two readout blocks, by extending the sampling to N≥2 readout blocks after a magnetization preparation 301. Having more readout blocks allows a more precise quantification of T1 values in the tissue of the biological object 106. Known in the art techniques might be used then to quantify T1 from the reconstructed images. For instance, T1 relaxation times might be estimated by directly fitting a model on two or more reconstructed images or by combining two or more reconstructed images and comparing the resulting voxel intensities to simulated intensities.

According to another preferred embodiment illustrated in FIG. 4, the different readout blocks R_i take place, e.g., start, one after the other in order to form a continuous readout block R_cont. In other words, instead of sampling the preparation recovery by small readout blocks temporally separated from each other as in the previous preferred embodiments, MRI data might be continuously sampled throughout the whole of continuous readout block R_cont with many subsequent excitation-pulses. Preferentially, R_cont is a continuous 3D radial readout employed during the whole recovery period separating two successive magnetization preparations, which—combined with a sliding-window or time-shifting reconstruction for acquiring each MRI signal S_i (i.e., each MRI dataset) at different recovery times T_i—might allow a reconstruction of an arbitrary number of original image data sets. Since each MRI signal is acquired using a short-T2 sensitive readout block, like UTE, ZTE, or single-point readout, the short-T2 MRI signal components can be detected and quantitatively mapped. Preferentially, an arbitrary number greater than or equal to two of such original data sets (MRI signal S_i) can be used to reconstruct quantitative T1 and PD maps of the observed biological part, including short-T2 signals. More specifically, FIG. 4 shows 3 temporal windows W1, W2, W3, wherein window W2 overlaps both W1 and W3, wherein for each window W_i, a readout block R_i sensitive to short-T2 signal is used for acquiring the corresponding signal S_i, each signal S_i being acquired at a different inversion time T_i, enabling the creation of 3 different images I_1, I_2, I_3 at the respective inversion times TI_1, TI_2, TI_3.

According to another preferred embodiment of the invention illustrated in FIG. 5, M≥1 gradient-echoes can be formed after each excitation pulse 501 of a readout block R_i (e.g., UTE or ZTE readout) by using M successive gradients or gradient echo sequences 502 enabling to acquire, for each gradient echo sequence, a subset S_i, j of MRI data at an echo time TE_j for the signal S_i, with j=1, . . . , M. Due to the T2* decay after the excitation, every echo at TE_j will have a different signal intensity. This allows to separate image information that comes from tissue with short and long T2* or the quantification of T2*. For example, it becomes possible to estimate T1 maps independently with data collected at a first and second echo. The T1 difference between these two maps is caused by the T1 of the tissue with short-T2 species under the assumption that the magnetization of short-T2 species decays between the echoes. Thanks to this technique, different readout blocks (e.g., single echo readout block, dual echo readout block, or multi echo readout block) can be used to sample different numbers of echoes, each at a different echo time TE_j.

For instance, the present method might comprise two inversion-recovery times T_1 and T_2 (i.e., N=2) and two echo times TE_1 and TE_2 (i.e., M=2), enabling to reconstruct four images I_i,j:
- a first image I_1,1 (T_1, TE_1) that is characterized by a strong T1 weighting—short-T2 signal sensitive;
- a second image I_1,2 (T_1, TE_2) that is characterized by a strong T1 weighting—short-T2 signal insensitive;
- a third image I_2,1 (T_2, TE_1) that is characterized by a low T1 weighting—short-T2 signal sensitive; and a fourth image I_2,2 (T_2, TE_2) that is characterized by a low T1 weighting—short-T2 signal insensitive.

These images I_i,j can then be used to estimate the T1 relaxation time of short-T2 signal tissues that are mixed with tissue of long-T2 signal. Optionally, the MP2RAGE method [3] might be used between images I_1,1 and I_2,1, and respectively images I_1,2 and I_2,2 for calculating two T1 maps. The differences in T1 between these two T1 maps are dominated by the different signal fraction of short-T2 magnetization in the different echoes. Alternatively, multiple compartment models can be directly fitted on the images I_i,j. Advantageously, acquiring more than 2 inversions and echoes improves such fitting.

It will be understood that other methods of post processing the reconstructed images or the acquired MRI signals S_i that use mathematical operations on the different contrasts to extract information about tissue with short-T2 relaxation time might be used. For example, T2* or phase information can be extracted from the multi-echo readout. More detailed examples are given in the following:

3D MP-2-UTE (N=2, M>1) with multi-echo readout and additional T2* fitting: If more than one echo is acquired, then the present invention makes the calculation of quantitative T2* maps in addition to different sets of quantitative T1 and PD maps with data acquired at each echo time possible. This enables notably an efficient and B1-corrected T1, PD and T2* mapping.

3D MP-2-UTE (N=2, M>1) with multi-echo readout and with additional evaluation of phase information: The change of the complex phase of the images across different echoes contains additional information. The present invention proposes to use the multi-echo readout to extract phase information, and using the latter to estimate variations in the main magnetic field (B0) or tissue susceptibility in species with short T2. This enables notably an efficient and B1-corrected T1, PD, phase, B0, and susceptibility (QSM) mapping.

To summarize, the present invention proposes to combine the concept of MP2RAGE with a 3D readout sensitive to short-T2 signal to get notably a B1-insensitive quantification of T1 relaxation time in tissue or biological objects characterized by a short-T2 relaxation time. Furthermore, the present invention proposes to use multiple echoes during the readout for improving the distinction between short-T2 and long-T2 contribution of the T1 relaxation within a same voxel. It finally proposes to extended this approach to N inversion- or saturation-recovery times and M echoes to allow for the fitting of multicompartment models.

The Following is a Summary List of Acronyms Used in the Above Description of the Invention:
  MRI magnetic resonance imaging
  MR magnetic resonance
  RF radio frequency
  GRE gradient echo
  UTE ultra-short echo time
  ZTE zero echo time
  SPI single-point imaging
  qMRI quantitative magnetic resonance imaging
  IR inversion recovery
  SE spin-echo
  TR repetition time
  T_i recovery time
  QSM quantitative susceptibility mapping
  TE echo time
  VFA variable flip angle
  AFI actual flip angle
  FID free induction decay
  SP spoiler gradient
  RO readout gradient
  RW rewinding gradient
  MP magnetic preparation The following is a list of citations appearing in the above description; where necessary for disclosure purposes, the citations are incorporated by reference:

[1] Weiger, M., et al., Short-T2 MRI: Principles and recent advances. Prog Nucl Magn Reason Spectrosc, 2019. 114-115: p. 237-270.

[2] Glasser, M. F., et al., The minimal preprocessing pipelines for the Human Connectome Project. NeuroImage, 2013. 80: p. 105-124.

[3] Marques, J. P., et al., MP2RAGE, a self bias-field corrected sequence for improved segmentation and T1-mapping at high field. NeuroImage, 2010. 49(2): p. 1271-1281.

[4] Du, J., et al., Qualitative and quantitative ultrashort echo time (UTE) imaging of cortical bone. J Magn Reson, 2010. 207(2): p. 304-11.

[5] Du, J. and G. M. Bydder, Qualitative and quantitative ultrashort-TE MRI of cortical bone. NMR in Biomedicine, 2013. 26(5): p. 489-506.

[6] Wei, Z., et al., To measure T1 of short T2 species using an inversion recovery prepared three-dimensional ultrashort echo time (3D IR-UTE) method: A phantom study. Journal of Magnetic Resonance, 2020. 314: p. 106725.

[7] Guo, T., et al., T1 measurement of bound water in cortical bone using 3D adiabatic inversion recovery ultrashort echo time (3D IR-UTE) Cones imaging. Magnetic Resonance in Medicine, 2020. 84(2): p. 634-645.

[8] Triphan, S. M. F., et al., Oxygen enhanced lung MRI by simultaneous measurement of T1 and T2* during free breathing using ultrashort TE. Journal of Magnetic Resonance Imaging, 2015. 41(6): p. 1708-1714.

[9] WielpOtz, M. O., et al., Outracing Lung Signal Decay-Potential of Ultrashort Echo Time MRI. Rofo, 2019. 191(05): p. 415-423.

[10] Beyea, S. D., et al., Relaxation Time Mapping of ShortT*2Nuclei with Single-Point Imaging (SPI) Methods. Journal of Magnetic Resonance, 1998.135(1): p. 156-164.

[11] Wei, Z., et al., Fast T1 measurement of cortical bone using 3D UTE actual flip angle imaging and single-TR acquisition (3D UTE-AFI-STR). Magnetic Resonance in Medicine, 2021. 85(6): p. 3290-3298.

[12] Springer, F., et al., Magnetization transfer contrast imaging in bovine and human cortical bone applying an ultrashort echo time sequence at 3 Tesla. Magnetic Resonance in Medicine, 2009. 61(5): p. 1040-1048

[13] Chen, J., et al., Measurement of bound and pore water T1 relaxation times in cortical bone using three-dimensional ultrashort echo time cones sequences. Magnetic Resonance in Medicine, 2017. 77(6): p. 2136-2145

[14] Ma, Y.-J., et al., Whole knee joint T1 values measured in vivo at 3T by combined 3D ultrashort echo time cones actual flip angle and variable flip angle methods. Magnetic Resonance in Medicine, 2019. 81(3): p. 1634-1644

[15] Li, Q., et al., Ultrashort echo time magnetic resonance fingerprinting (UTE-MRF) for simultaneous quantification of long and ultrashort T2 tissues. Magnetic Resonance in Medicine, 2019. 82(4): p. 1359-1372.

The invention claimed is:

1. A magnetic resonance imaging (MRI) method for mapping, with an MRI system, T1 relaxation times of a biological object having a part that is characterized by a short-T2 relaxation time, the method comprising:

performing, by the MRI system, one or a plurality of magnetization preparation radio frequency (RF) pulse sequences, with two successive magnetization preparation RF pulse sequences being separated by a repetition time interval TR;

acquiring, by the MRI system and during each repetition time interval TR, an MRI signal generated by the part of the biological object in response to a number N of 3D readout blocks R_i generated by the MRI system and applied to the part of the biological object, wherein for each readout block R_i, an MRI signal S_i is acquired by the MRI system at a different recovery time T_i, and wherein each readout block R_i is configured to be sensitive to short-T2 signal, and wherein i=1, . . . , N, and N≥2; and reconstructing, from each MRI signal S_i at various T_i, an image of the part and mapping T1 values for the part from two or more of the reconstructed images.

2. The MRI method according to claim 1, which comprises separating each readout block R_i from a next readout block R_i+1, and thereby separating the acquired signal S_i from a next-acquired signal S_i+1, by a time interval greater than 0.

3. The MRI method according to claim 1, wherein the N readout blocks form a continuous readout excitation pulse sequence R_cont configured for execution by the MRI system, wherein the MRI signals S_i are acquired at different recovery times T_i in order to create images with many different T_i.

4. The MRI method according claim 1, wherein each readout block R_i comprises a train of RF excitation pulses of predefined flip angle, each followed by M gradient echoes resulting in an additional dimension in the MRI signal denoted as S_i,j, with i=1, . . . , N, with N≥2 and j=1, . . . , M, with M≥1.

5. The MRI method according to claim 1, wherein each readout block comprises:

one or more RF excitations with UTE signal readouts; or one or more RF excitations with ZTE signal readouts; or one or more RF excitations with SPI data-point collections.

6. The MRI method according to claim 1, wherein the magnetization preparation RF pulse sequence is an inversion or saturation recovery pulse sequence.

7. The MRI method according to claim 1, which comprises combining the two or more reconstructed images for extracting information about biological object tissue with short-T2 relaxation time.

8. The MRI method according to claim 1, which comprises extracting T1 and T2* information directly from the two or more reconstructed images by a fitting of an analytical model.

9. The MRI system configured for carrying out the MRI method according to claim 1.

* * * * *